(12) United States Patent
Huang et al.

(10) Patent No.: US 8,795,179 B2
(45) Date of Patent: Aug. 5, 2014

(54) METHODS, MODULES, AND SYSTEMS FOR GAIN CONTROL IN B-MODE ULTRASONIC IMAGING

(75) Inventors: Yong Huang, Shenzhen (CN); Jing Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 147 days.

(21) Appl. No.: 13/085,297

(22) Filed: Apr. 12, 2011

(65) Prior Publication Data

US 2012/0260736 A1   Oct. 18, 2012

(51) Int. Cl.
 *A61B 8/00*   (2006.01)
 *G01S 15/89*   (2006.01)
 *G01S 7/52*   (2006.01)

(52) U.S. Cl.
 CPC ......... *G01S 15/8981* (2013.01); *G01S 7/52033* (2013.01); *G01S 7/52026* (2013.01)
 USPC .............................. 600/443; 600/447; 600/437

(58) Field of Classification Search
 None
 See application file for complete search history.

(56) References Cited

U.S. PATENT DOCUMENTS

| | | | | |
|---|---|---|---|---|
| 4,106,054 A | * | 8/1978 | Tzakis | 348/648 |
| 4,458,689 A | * | 7/1984 | Sorenson et al. | 600/447 |
| 4,476,873 A | * | 10/1984 | Sorenson et al. | 600/447 |
| 4,489,729 A | * | 12/1984 | Sorenson et al. | 600/447 |
| 4,596,144 A | * | 6/1986 | Panton et al. | 73/620 |
| 4,841,301 A | * | 6/1989 | Ichihara | 341/126 |
| 5,042,499 A | * | 8/1991 | Frank et al. | 600/511 |
| 5,241,310 A | * | 8/1993 | Tiemann | 341/143 |
| 5,255,093 A | * | 10/1993 | Topper et al. | 348/255 |
| 5,314,663 A | | 5/1994 | Mimura | |
| 5,327,894 A | * | 7/1994 | Thomas | 600/454 |
| 5,349,524 A | * | 9/1994 | Daft et al. | 600/441 |
| 5,349,525 A | * | 9/1994 | Dunki-Jacobs et al. | 600/437 |
| 5,827,479 A | | 10/1998 | Yamazaki et al. | |
| 6,120,446 A | * | 9/2000 | Ji et al. | 600/437 |
| 6,321,073 B1 | * | 11/2001 | Luz et al. | 455/239.1 |
| 6,398,733 B1 | * | 6/2002 | Simopoulos et al. | 600/443 |
| 7,065,335 B2 | * | 6/2006 | Ben-Ayun et al. | 455/240.1 |
| 7,386,074 B1 | * | 6/2008 | Venkatesh et al. | 375/345 |
| 7,409,018 B2 | * | 8/2008 | Kim | 375/345 |
| 2003/0186665 A1 | * | 10/2003 | Black et al. | 455/240.1 |
| 2003/0207674 A1 | * | 11/2003 | Hughes | 455/234.1 |
| 2003/0236459 A1 | * | 12/2003 | Loftman et al. | 600/437 |
| 2004/0009758 A1 | * | 1/2004 | Graham et al. | 455/234.1 |
| 2006/0159587 A1 | | 7/2006 | Fechtner et al. | |
| 2007/0164898 A1 | * | 7/2007 | Pan et al. | 342/104 |
| 2007/0167780 A1 | * | 7/2007 | Imamura et al. | 600/443 |
| 2008/0154131 A1 | * | 6/2008 | Lee et al. | 600/439 |
| 2008/0189104 A1 | * | 8/2008 | Zong et al. | 704/226 |
| 2009/0299184 A1 | * | 12/2009 | Walker et al. | 600/447 |
| 2010/0045497 A1 | * | 2/2010 | Chandra | 341/139 |
| 2010/0069755 A1 | * | 3/2010 | Nishimura et al. | 600/443 |
| 2010/0150468 A1 | * | 6/2010 | Ali | 382/266 |

FOREIGN PATENT DOCUMENTS

| | | |
|---|---|---|
| CN | 1963527 | 5/2007 |
| CN | 201035026 | 3/2008 |
| EP | 1380841 A2 | 1/2004 |
| JP | 2005099059 | 4/2005 |

\* cited by examiner

*Primary Examiner* — Nicholas Evoy
(74) *Attorney, Agent, or Firm* — Kory D. Christensen; Stoel Rives LLP

(57) ABSTRACT

A gain control method for B-mode ultrasonic imaging, a gain control module, and a B-mode ultrasonic imaging system are disclosed.

15 Claims, 6 Drawing Sheets

A (N1-25, S1-55, S2-70, S3-85, S4-100)

B (N1-45, S1-75, S2-90, S3-105, S4-120)

C (N1-65, S1-95, S2-110, S3-125, S4-140)

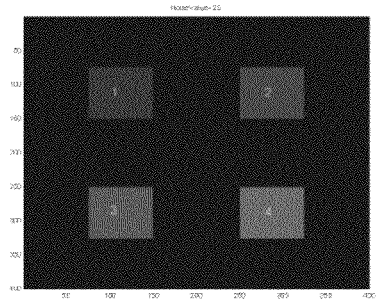
A1(Noise-25, 1-55, 2-70, 3-85, 4-100)
FIG. 9A1
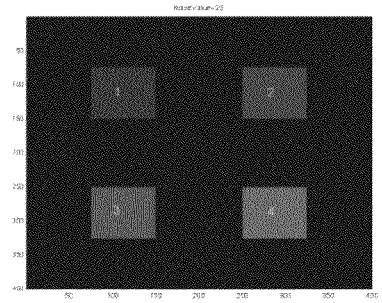
B1(Noise-25, 1-55, 2-70, 3-85, 4-100)
FIG. 9B1
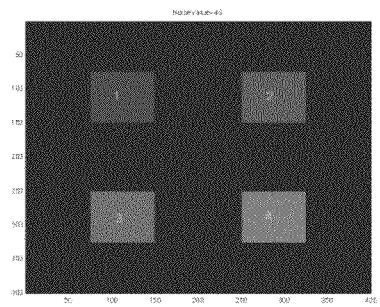
A2(Noise-45, 1-75, 2-90, 3-105, 4-120)
FIG. 9A2
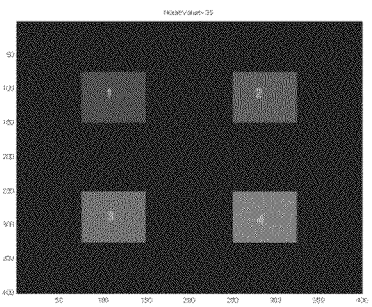
B2(Noise-35, 1-75, 2-90, 3-105, 4-120)
FIG. 9B2
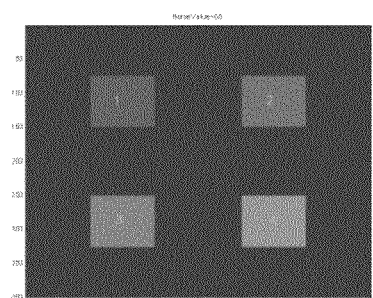
A3(Noise-65, 1-95, 2-110, 3-125, 4-140)
FIG. 9A3
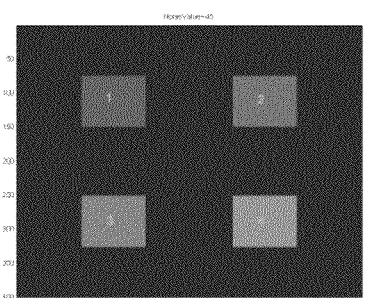
B3(Noise-45, 1-95, 2-110, 3-125, 4-140)
FIG. 9B3

METHODS, MODULES, AND SYSTEMS FOR GAIN CONTROL IN B-MODE ULTRASONIC IMAGING

TECHNICAL FIELD

The present disclosure relates to ultrasonic imaging and, more particularly, to gain control in B-mode ultrasonic imaging.

BRIEF DESCRIPTION OF THE DRAWINGS

FIGS. 9A1, 9A2, 9A3, 9B1, 9B2 and 9B3 contrast between a grayscale view obtained by processing using a gain control method of the present disclosure and a grayscale view obtained by conventional processing.

DETAILED DESCRIPTION

A medical diagnostic ultrasonic imaging system generates ultrasound images of tissue by emitting ultrasound to the tissue and then receiving reflected echo signals. The energy of an ultrasonic signal gradually attenuates in increased transmission distance, and the attenuation is inconsistent with different tissues and different depths. Currently, a typical B-mode ultrasonic imaging system generally has a digital gain control, which is usually implemented by multiplying the echo signal by a fixed gain value, so as to amplify the signal to the appropriate amplitude for observation.

As the ultrasonic echo signal has a wide dynamic scope, and mainly the weak signals have meaning in clinical diagnosis, in order to facilitate observation in a B-mode ultrasonic imaging system, a logarithmic compression process is added. However, raw data undergoes the logarithmic compression process after the gain control, and if the gain value is greater than 1, a signal to noise ratio (SNR) of the output signal is caused to be lower than the SNR of the primary signal; if the gain is less than 1, though the SNR of the output signal may be increased, weak signal components of the input signal decline too fast, such that this part of the information is covered by the noise signal and then lost.

Figure 1A:
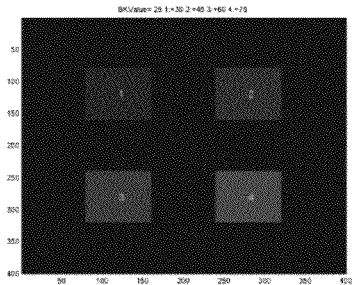
FIGS. 1A, 1B, and 1C are schematic contrast views of a grayscale effect obtained by using a linear gain control processing method.
Figure 1B:
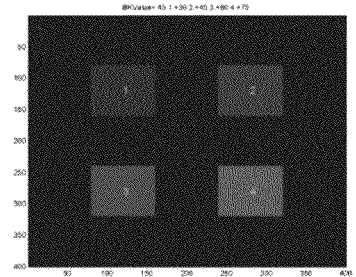
Figure 1C:
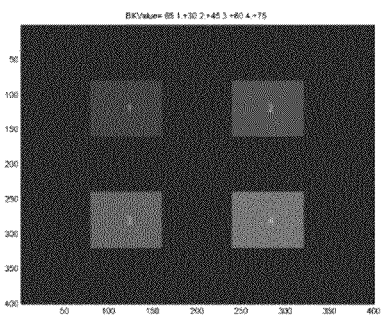

Referring to FIGS. 1A to 1C, in each figure, the background represents the noise signal, four small blocks respectively represent imaging signals having different grayscales, in which the signal that is least prominent against the background (or most similar to the background) at the upper-left may represent the small signal part of the signal. FIG. 1B is a schematic grayscale view of a primary input signal; FIG. 1A is a schematic grayscale view of various signals in FIG. 1B after a gain of less than 1 and the logarithmic process; and FIG. 1C is a schematic grayscale view of various signals after the gain of greater than 1 and the logarithmic process.

What may be seen is that the contrast of FIG. 1C declines significantly as compared to FIG. 1B, which indicates that the SNR decreases; although the SNR in FIG. 1A increases, the small signal part decreases significantly against the background and is not easy to distinguish, and this part of the information is possible to lose. Whether the SNR decreases or the small signal part declines too fast, the quality of the output image decreases, resulting in difficult recognition.

It can be seen from the above that conventional gain control methods of B-mode ultrasonic systems have the following two problems:

1) When the gain increases, the SNR of the image data declines, and a visual SNR decreases significantly.

2) When the gain decreases, the image brightness changes unevenly, the image darkens fast, and the diagnosis information is quickly lost.

The present disclosure is directed to a gain control method for B-mode ultrasonic imaging, such that when the gain is greater than 1, a SNR of image data may be maintained essentially unchanged; or when the gain decreases, the decline of the background noise and imaging signal is gradual and the whole brightness of the image changes evenly, thus avoiding the rapid loss of image brightness and information.

The present disclosure is further directed to a gain control module implemented by using the gain control method for B-mode ultrasonic imaging, and a B-mode imaging system implemented by using the improved gain control module.

In one embodiment, a gain control method for B-mode ultrasonic imaging includes the following steps:

A. judging background noise and imaging signal in image data before gain to obtain a background noise threshold and a signal threshold;

B. setting a nonlinear gain curve at an interval from image data 0 before gain to the signal threshold; when a standard gain is greater than 1, enabling a first gain at an interval from the data 0 to the background noise threshold to be less than the standard gain and greater than 1, and a gain at an interval from the background noise threshold to the signal threshold to be greater than the standard gain; and when the standard gain is less than 1, enabling a second gain at the interval from the data 0 to the background noise threshold to be greater than the standard gain and less than 1, and the gain at the interval from the background noise threshold to the signal threshold to be less than the standard gain.

Based on the above-described method, the present disclosure further provides a gain control module for B-mode ultrasonic imaging, which includes a threshold setting module and a gain processing module interconnected to each other. The threshold setting module is used to collect signal amplitude of input image data and set a signal threshold and a background noise threshold according to amplitude scopes of the signal and the noise. The gain processing module is used to perform a nonlinear gain control on the input image data, and when a standard gain is greater than 1, control the gain at an interval from image data 0 to the background noise threshold to be less than the standard gain and greater than 1, and control the gain at an interval from the background noise threshold to the signal threshold interval to be greater than the standard gain; and when the standard gain is less than 1, control the gain at the interval from the image data 0 to the background noise threshold to be greater than the standard gain and less than 1, and control the gain at the interval from the background noise threshold to the signal threshold interval to be less than the standard gain.

The present disclosure further provides a B-mode imaging system, which includes a B signal processing module using the above-described B-mode imaging gain control module.

In one embodiment, the methods, devices, and systems of the present disclosure judge the background noise threshold and the signal threshold before gain to set different threshold intervals for the background noise and the signal, and use different nonlinear gain control methods in different threshold intervals. In this way, when the gain increases, the SNR of the image data is maintained essentially unchanged, solving the problem of significantly decreased visual SNR. When the gain decreases, the decline of the background noise and imaging signal is gradual, and the SNR of the image data is maintained essentially unchanged, and whole image brightness changes evenly, making the output image clearer.

Figure 2:
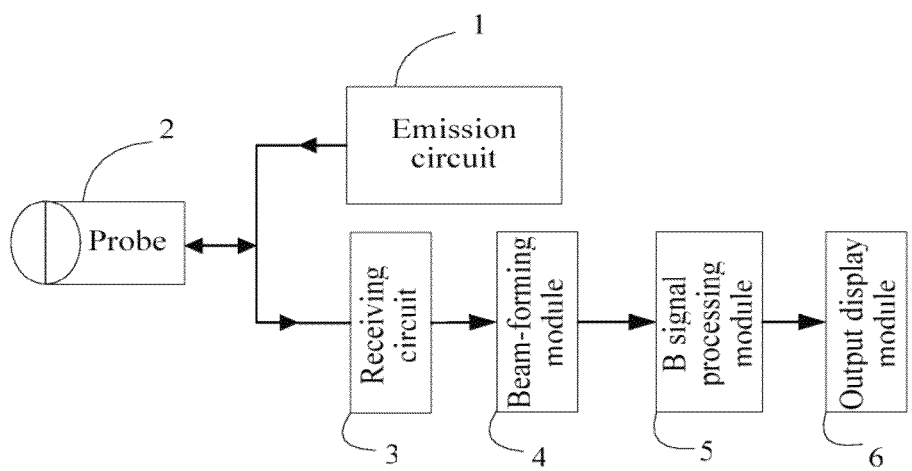
FIG. 2 is a block diagram of a B-mode ultrasonic diagnosis system.

Various embodiments of the present disclosure are now described in detail with reference to the accompanying drawings. As shown in FIG. 2, an embodiment of a B-mode imaging system includes an emission circuit 1, a probe 2, a receiving circuit 3, a beam-forming module 4, a B signal processing module 5, and an output display module 6. The emission circuit 1 is used to generate a voltage for exciting array elements of the probe to emit ultrasound waves. Different array elements usually require different emission voltages and emission delays, and the emission circuit 1 generates different emission voltages and delays for each array element according to usage requirements.

The probe 2 includes a plurality of array elements, and each array element generates an ultrasound wave having a certain frequency band under the excitation of the emission voltage. The ultrasound wave returns to the probe array elements after being reflected by the tissue, and the array element converts an echo signal to an electrical signal. The receiving circuit 3 may include one or more channels, and can be responsible for performing processes, such as amplification and analog to digital (A/D) conversion, on the electrical signal obtained by the probe 2, and output the converted digital signal for subsequent processes. The beam-forming module 4 may be used for adding a delay of data output from each channel of the receiving circuit 3 to synthesize data of different scan lines for output. The output signal is usually referred to an RF signal. The B signal processing module 5 may be used for processing the RF signal output by the beam-forming module 4. The output display module 6 may be used for displaying the data output by the B signal processing module 5 as an image.

Figure 3:
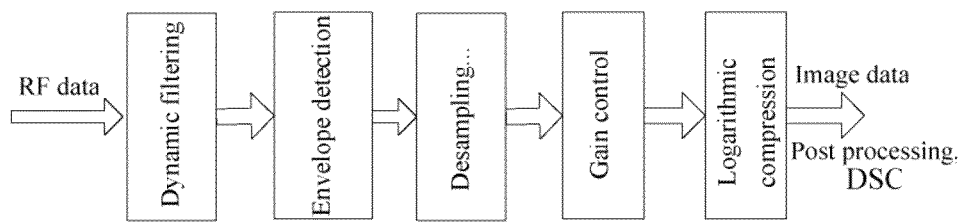
FIG. 3 is a schematic flow chart of processing a radio frequency (RF) signal by a signal processing module in a B-mode ultrasonic diagnosis system.

As shown in FIG. 3, the main processing steps of the B signal processing module 5 may include dynamic filtering, envelope detection, desampling, digital gain compensation, logarithmic compression, and dynamic scope adjustment, so that the RF signal can be converted to an unsigned number of 8 bits to output. The digital gain compensation amplifies the signal to an amplitude appropriate for observation, so as to compensate for the influence of inconsistent attenuation generated by the ultrasound transmission in different tissues and with different depths. The logarithmic compression process facilitates observing weak signals having a clinical diagnosis meaning in the ultrasonic echo signal. When the gain control is synthesized with the logarithmic compression, a synthetic expression can be described as a formula (1):

$$\text{dataOut}=k*(\log a(\text{dataIn}*\text{Gain})+b) \quad (1)$$

where dataIn represents the input signal, dataOut represents the output signal and may be considered as the image data, Gain represents the digital gain, and straight through has the gain of 1. The coefficients a, b, and k vary with different system designs, but can be fixed as for a specific ultrasonic imaging system. The formula (1) may be converted to a formula (2) after an operation of log conversion:

$$\text{dataOut}=k*\log a(\text{dataIn})+k*\log a(\text{Gain})+k*b \quad (2)$$

Under a determined working condition (without user adjustment), k, a, b are all constants, Gain is a gain curve set according to different areas to which the data before gain belongs, that is, the gain control in this embodiment uses a nonlinear gain control method. What can be seen from the formula (2), is that adjusting Gain actually performs an addition operation on the image data.

Figure 4:
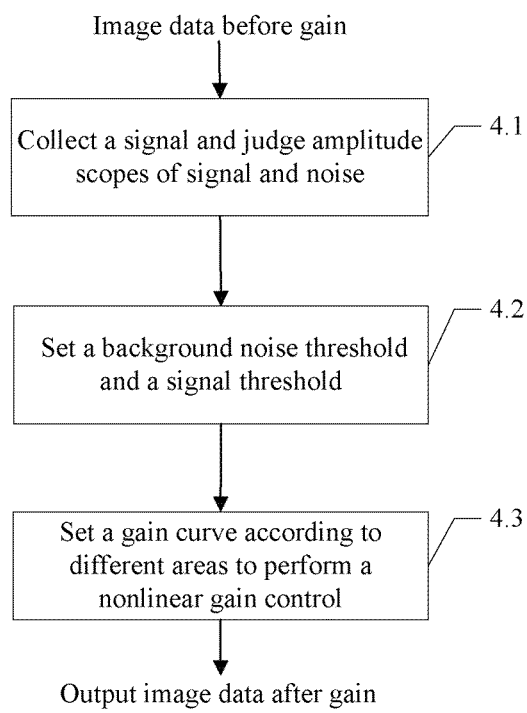
FIG. 4 is a schematic flow chart of a nonlinear gain control method for B-mode imaging.

A nonlinear gain control method for B-mode imaging according to an embodiment of preset disclosure is shown in FIG. 4, and may include the following steps.

In Step 4.1, collecting signal amplitude of a blind area and a signal area of an image signal before gain, and judging to obtain amplitude scopes of signal and noise.

In Step 4.2, a background noise threshold and a signal threshold are set to set different threshold intervals for the background noise and imaging signal.

In Step 4.3, a gain curve is set area by area to perform a nonlinear gain control on the data before digital gain. Specifically, when the gain is amplified (that is, Gain>1), the gain below the background noise threshold can be appropriately decreased, the gain between the background noise threshold and the signal threshold can be appropriately increased, and the gain above the signal threshold remains unchanged. In this way, when the gain is amplified, the increase of the background noise is less than the increase of the signal, and a SNR is maintained to be basically unchanged. On the other hand, when the gain decreases (that is, Gain<1), the gain below the background noise threshold can be appropriately increased, the gain between the background noise threshold and the signal threshold can be appropriately decreased, and the gain above the signal threshold remains unchanged. In this way, when the gain is decreased, decline of the background noise and the signal is relatively gradual, and the SNR is maintained essentially unchanged, such that the whole image brightness changes evenly at the same time.

Figure 5:
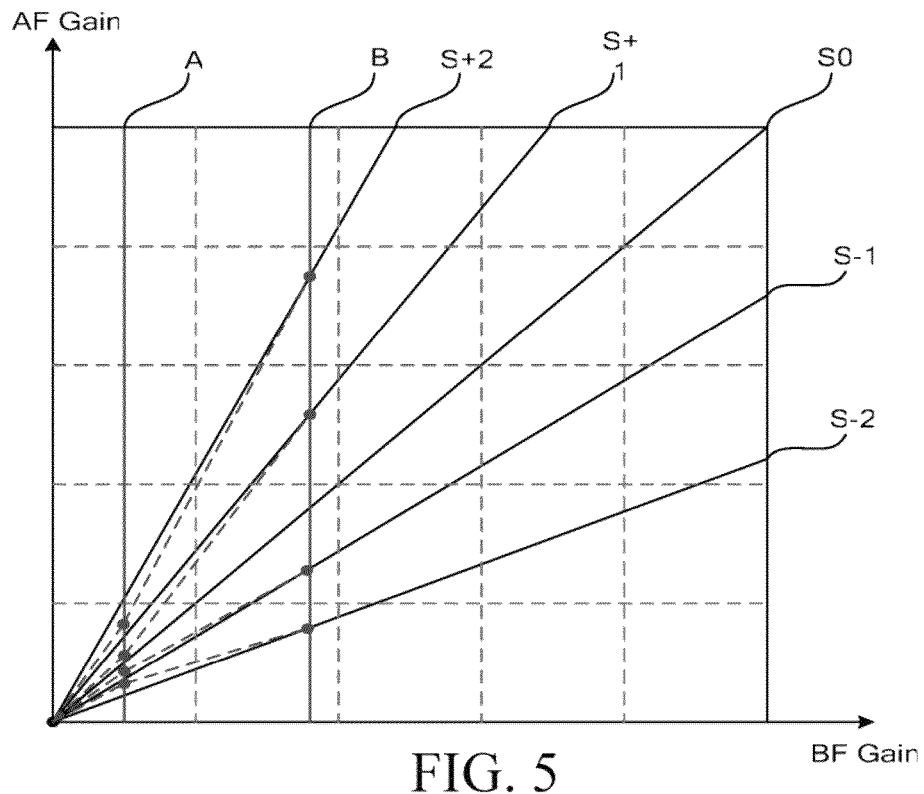
FIG. 5 is a schematic view of a gain curve produced by a nonlinear gain control method.

Referring to FIG. 5, a horizontal axis represents image data before gain (BF gain) and a vertical axis shows image data after gain (AF gain). In FIG. 5, a slope of a gain curve represents a gain value. For example, S0 represents the gain curve having the gain of 1, S+1 and S+2 represent linear gain curves having the gain greater than 1, that is, increasing gains, S−1 and S−2 represent linear gain curves having the gain less than 1, that is, decreasing gains. According to amplitude scopes of a signal and noise before gain, a lower limit threshold A (that is a background noise threshold) and an upper limit threshold B (signal threshold) are set for the data before gain; and the data before gain is divided into three areas, that is, an interval from data 0 to the background noise threshold (0 A], an interval from the background noise threshold to the signal threshold [A B], and an interval greater than the signal threshold [B max).

The gain is set according to different areas. As for the data greater than the upper limit threshold B [B max), a manner of a standard gain is maintained. The standard gain means the gain is kept as the slope of the S+1, S−2, S+3 and S+4 gain curves, respectively. As for the data less than the lower limit threshold A, when the standard gain is greater than 1 (Gain>1), for example, the gain curves S−1 and S+2 shown in FIG. 5, the gain value is decreased (that is, decreasing the slope) on the basis of the standard gain according to an appropriate proportion, so as to enable the gain to be less than the standard gain and greater than 1. When the standard gain is less than 1 (Gain<1), for example, the gain curves S+1 and S+2 shown in FIG. 5, the gain is increased (that is, increasing the slope) on the basis of the standard gain according to an appropriate proportion, so as to enable the gain to be greater than the standard gain and less than 1.

As for the data between the lower limit threshold A and the upper limit threshold B, a gain curve is modified with a linear interpolation method or a curve fitting method according to the slope of the gain curve within intervals (0 A] and [B max), so that when the standard gain is greater than 1, the gain at the interval [A B] is greater than the standard gain, and when the standard gain is less than 1, the gain at the interval [A B] is less than the standard gain. In FIG. 5, a dashed curve is a nonlinear gain curve at the interval from the image data 0 to the signal threshold.

What may be found from the formula (2) that, when user turns up or turns down the gain, a variable is increased or decreased on the image data. A conventional medical ultrasonic image usually includes the background noise having a smaller signal value and an imaging signal having a bigger signal value, in which the imaging signal is the part required to observe, and the background noise is an unnecessary interference signal which influences the observation on the imaging signal. It is assumed that a mean value of the background noise is N, a mean value of signal of the imaging signal is S, and if all signals use the same Gain for adjusting the gain, the noise signal and imaging signal output after being processed by a logarithmic compression module equal to increasing or decreasing the same amount on S and N respectively.

More specifically, assuming that under an initial state, $S1=75$, $N1=45$, a SNR of an initial image is $SNR=S1/N1=1.67$, an increasing gain satisfies $k*loga (Gain)=20$, after increasing the gain, $S1'=75+20=95, N1'=45+20=65$, at this time, the SNR of the image is $SNR'=S1'/N1'=1.46$. Clearly, $SNR'<SNR$, and the SNR appears to decline. The nonlinear gain method in this implementation performs the gain control according to different intervals on the input signal. When the gain is greater than 1 (that is when the gain increases), in the image data, an increase value of the background noise signal is less than the increase value of the imaging value, so as to eliminate a problem of decline of the SNR of the image data in the prior art. When the gain is less than 1 (that is when the gain decreases), in the image data, a decrease value of the background noise signal is less than the decrease value of the imaging value, the value of the SNR of the image data is decreased in comparison with the standard gain, but still is greater than the SNR of the image data before gain. More importantly, rapid loss of the image brightness and information is avoided, as well as uneven changes in image brightness. Therefore, the nonlinear gain control method of the present disclosure enables the output image to be clearer, and diagnostic accuracy is increased.

In some embodiments, the lower limit threshold A (background noise threshold) and the upper limit threshold B (signal threshold) may be set by using the following method.

1. The signal amplitude of a blind area and signal area of the image signal before gain is collected and judged to obtain the amplitude scopes of the signal (Smin Smax) and the amplitude scopes of the noise (0 Nmax), in which Nmax represents a maximum value of the background noise, Smin represents a minimum value of the signal, Smax represents a maximum value of the signal, and both Nmax<Smin or Nmax>Smin is possible.

2. The background noise threshold can be set to be any value at a closed interval [Smin, Nmax] or [Nmax, Smin], and the signal threshold can be set to be the maximum value of the signal multiplied by L (that is, Smax*L), in which L can be any number from 0 to 2, and it can be set according to different B-mode ultrasonic systems, e.g., L may be set to be $L=1\pm0.2$. In some embodiments, the background noise threshold may be set by using multiple methods. For example, the maximum value of the background noise can be compared with the minimum value of the signal, and the maximum value of the two can be set to be the background noise threshold, or the maximum background noise value can be compared with the minimum signal value, and the minimum value of the two can be selected to be set as the background noise threshold. In some other embodiments, the maximum value of the background noise or the minimum value of the signal can be directly to be set as the background noise threshold without comparing the maximum value of the background noise and the minimum value of the signal, or any number at an interval determined by the background noise maximum value and the signal minimum value can be selected to serve as the background noise threshold.

Some exemplary methods for setting the nonlinear gain control curve are described in the following embodiments.

Figure 6:
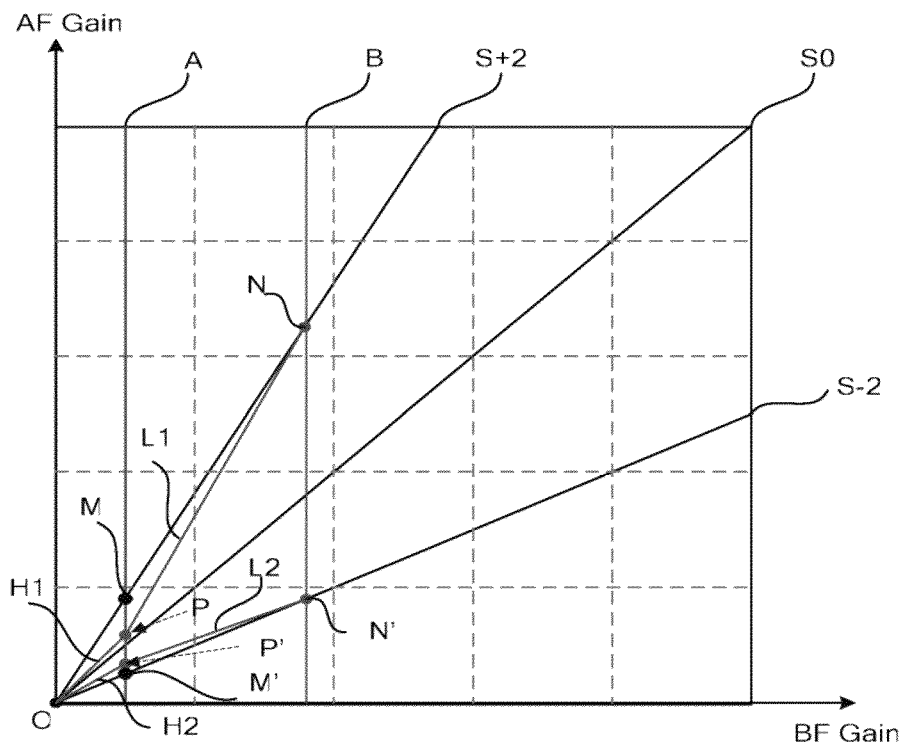
FIG. 6 is a schematic view of a nonlinear gain curve obtained by using an interpolation method.

As shown in FIG. 6, a standard gain curve is obtained according to a required standard gain value, such as S+2 and S−2 in FIG. 6. A background noise threshold line (line A) and a signal threshold line (line B) are obtained by respectively drawing a perpendicular line from a background noise threshold A and a signal threshold B to a horizontal axis (BF Gain axis), and the lines A and B respectively intersect with the standard gain curve S+2 at points M and N. Assuming that a gain value of S+2 at this time is K1 (K1>1), that is a slope of S+2 curve is K1, the gain of the gain curve less than threshold A is decreased (that is, the slope is decreased); assuming that the decreased gain is a first gain K2, $k2=k1*m$, where m is a decimal and satisfies $m\leq1$ and $k1*m\geq1$. At this time, a gain curve H1 at an interval from image data 0 to the background noise threshold is obtained by drawing a line with K2 to be the slope and 0 point to be the origin. The gain curve H1 intersects with the line A to obtain another point P, and a gain curve at the interval [A, B], that is, a modified curve L1 can be obtained by connecting the point P to the point N with a linear interpolation method. The line H1 having the slope of K2 at the interval (0 A], the line L1 at the interval [A B], and the standard gain curve S+2 at the interval [B max) together form a new nonlinear gain curve.

It is similar to obtain a nonlinear gain curve when the gain is decreased or the standard gain is lower than 1. For example, the standard gain curve before modification is S−2, and lines A and B respectively intersect with the standard gain curve S−2 at points M' and N'. Assuming that the gain value of S−2 at this time is k3 (k3<1), that is, the slope of S−2 curve is k3, the gain of the gain curve less than threshold A is increased (that is, the slope is increased). Assuming that the increased gain is a second gain k4, where $k3<k4\leq1$, at this time, a gain curve H2 can be obtained at the interval from the image data 0 to the background noise threshold by drawing a line with the slope of k4 and the origin of 0 point. The gain curve H2 intersects with the line A to obtain another point P', a gain curve at the interval [A, B], that is, a modified curve L2 can be obtained by directly connecting the points P' and N' with a linear interpolation method. In this embodiment, the gain curves H1 and H2 are less than threshold A interval and the gain curves L1 and L2 at the interval from the threshold A to the threshold B are lines obtained by using the linear interpolation method.

Figure 7:
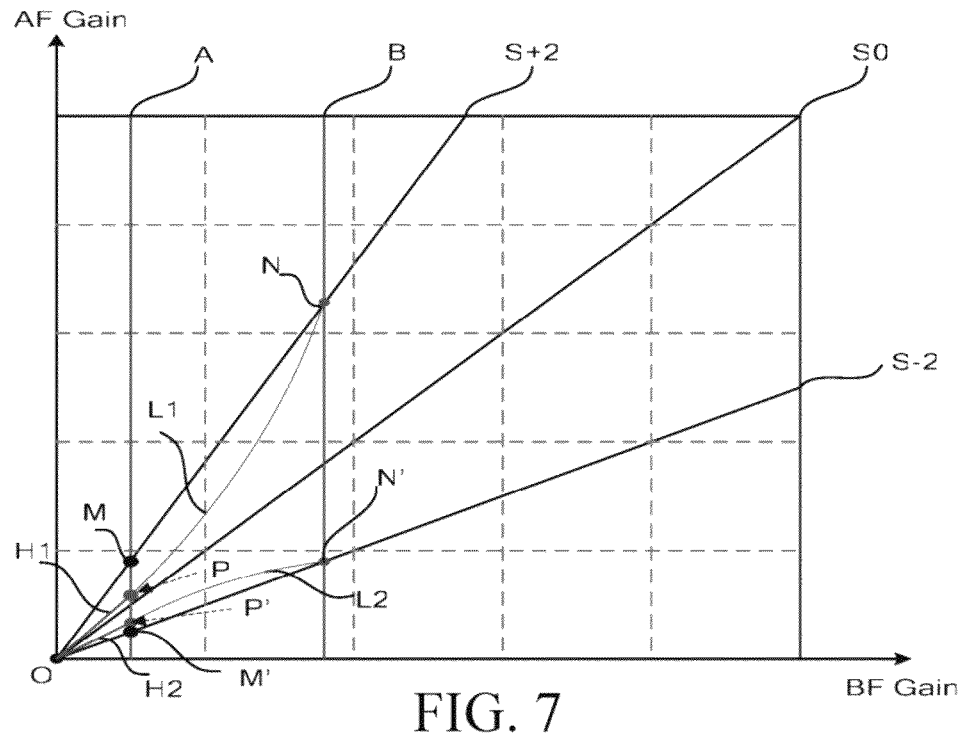
FIG. 7 is a schematic view of a nonlinear gain curve obtained at an interval from a background noise threshold to a signal threshold by using a curve fitting method.

As shown in FIG. 7, an method of obtaining the first gain curves H1 and H2 at the interval less than the threshold A is similar to that in the first embodiment, the major difference of this embodiment is that the curves L1 or L2 fitted by two points of the first intersection P and the second intersection N or the first intersection P' and the second intersection N' serves as the gain curve at the interval from the threshold A to the threshold B, and the fitting method may be nonlinear. The line H1 having the slope of K2 at the interval (0 A], the line L1 at the interval [A B], and the standard gain curve S+2 at the interval [B max) together form a new nonlinear gain curve. In a similar way, when the gain is decreased, the modified gain curve includes the line H2 at the interval (0 A], the curve L2 at the interval [A B], and the standard gain curve S−2 at the interval [B max).

Figure 8:
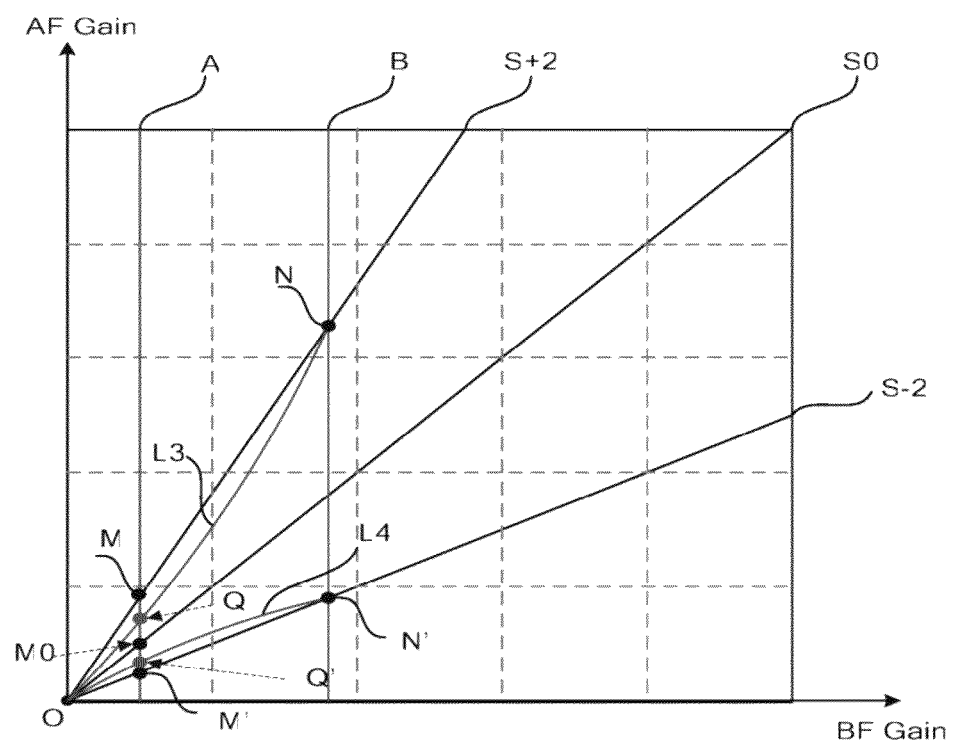
FIG. 8 is a schematic view of a nonlinear gain curve obtained at an interval from data 0 to the signal threshold by using a curve fitting method.

As shown in FIG. 8, a standard gain curve is obtained according to a required standard gain value, such as S+2 and S−2 in FIG. 6. A background noise threshold line (line A) and a signal threshold line (line B) can be obtained by respectively drawing a perpendicular line from a background noise threshold A and a signal threshold B to a horizontal axis (BF Gain axis), and the lines A and B respectively intersect with the standard gain curve S+2 at points M and N. An intersection between a zero gain curve S0 having the gain of 1 and A is signed as a fourth intersection M0. As for data at the interval [0 A], a point Q can be selected between the point M and the point M0 on the line A, and the point Q satisfies AF Gain_M0≤AF Gain_Q≤AF Gain_M, that is, the position of Q can be adjustable between the point M and the point M0. Then, a curve L3 can be fitted according to three points including an origin O of the coordinate axis, the point Q, and the point N, and L3 is a new gain curve at an interval [0,B], in which the method of curve fitting may be a linear fitting method or a nonlinear fitting method. Similarly, when the gain is decreased, the difference can be only that a point Q' on the line A is selected below the M0 and a point M' (an intersection between the standard gain curve S−2 and the threshold A). In this embodiment, the gain curves before modification and after modification are respectively as shown by S−2 and L4 in FIG. 8.

In the above or following descriptions, both the points M and M' can be called a third intersection, both the points N and N' can be called a second intersection, both the points P and P' can be called a first intersection, both the points Q and Q' can be called a fifth intersection, and both the gain curves H1 and H2 can be called a first gain curve.

As shown in FIG. 8, a first gain curve at an interval less than threshold A may also be obtained by using a curve fitting method. It is similar to the third embodiment. For example, a background noise threshold line (line A) and a signal threshold line (line B) can be obtained by respectively drawing a perpendicular line from a background noise threshold A and a signal threshold B to a horizontal axis (BF Gain axis), and the lines A and B intersect with a standard gain curve S+2 at points M and N. An intersection between a zero gain curve S0 having the gain of 1 and A is a fourth intersection M0. As for data at the interval [0 A], a point Q can be selected between the point M and the point M0 on the line A, and the point Q satisfies AF Gain_M0≤AF Gain_Q≤AF Gain_M. That is, the position of Q is adjustable between the point M and the point M0. A curve can be fitted according to two points of the origin O of the coordinate axis and Q, so as to obtain the gain curve at an interval from image data 0 to the background noise threshold. Similarly, when the gain is decreased, the difference may be only that the point Q' on line A is selected between below of the M0 and the point M'.

Figure 10:
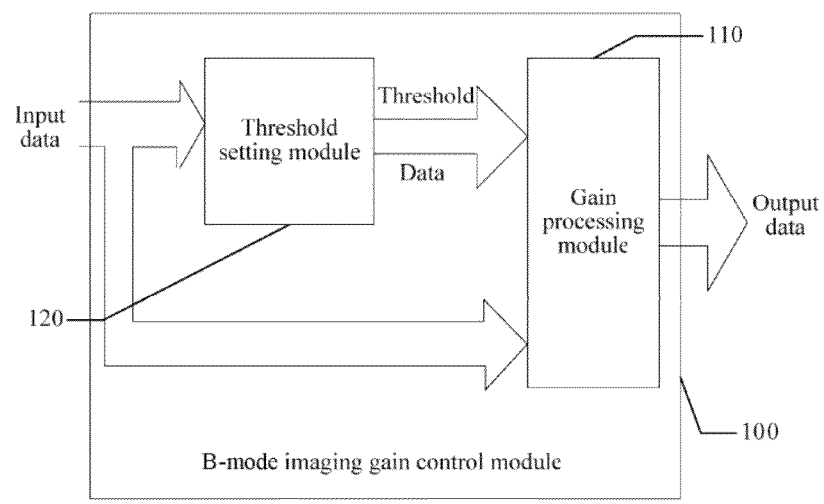
FIG. 10 is a block diagram of a gain control module.

As shown in FIG. 10, a B-mode imaging gain control module may be implemented using the above-described method includes a threshold setting module 120 and a gain processing module 110. The module may be implemented in hardware or software, or any suitable combination thereof. For example, the module may be implemented, in one embodiment, using a processor coupled to a memory storing instructions to perform the method. Input ends of the threshold setting module 120 and the gain processing module 110 are both connected with input image data before gain, and an output end of the threshold setting module 120 is connected to the gain processing module 110. The threshold setting module 120 can be used to collect signal amplitudes of the input image data, determine the amplitude scopes of the signal and noise, and set a signal threshold and a background noise threshold according to the amplitude scopes of the signal and noise, and output to the gain processing module 110 at the same time. The gain processing module 110 can be used to perform a nonlinear gain control on the input image data, and when a standard gain is greater than 1, control the gain at an interval from data 0 to the background noise threshold to be less than the standard gain and greater than 1, and control the gain at an interval from the background noise threshold to the signal threshold to be greater than the standard gain; or when the standard gain is less than 1, control the gain at the interval from the data 0 and the background noise threshold to be greater than the standard gain and less than 1, and control the gain at the interval from the background noise threshold and the signal threshold to be less than the standard gain; and output the image data after gain.

A B-mode ultrasonic imaging system may be implemented using the disclosed B-mode ultrasonic imaging gain control module. As shown in a block diagram of a system in FIG. 1, the difference can be that a digital gain compensation module in a B signal processing module 5 may use a B-mode imaging gain control module 100 as shown in FIG. 10.

FIGS. 9A1, 9A2, and 9A3 are grayscale views obtained by using the conventional linear gain control method; and FIGS. 9B1, 9B2, and 9B3 are grayscale views obtained by using the nonlinear gain control method according to the present disclosure. The grayscale difference values of the background of FIGS. 9A1 and 9B1, four blocks of signal areas (1, 2, 3, and 4), and the background area are consistent. In FIGS. 9A1, 9A2, and 9A3, a linear gain method is used, and the grayscale value of the background gain and four blocks of signal areas increase 20 each time; while in FIGS. 9B1, 9B2, and 9B3, a nonlinear gain control method is used, the grayscale value of the background gain increases 10 each time and the grayscale value of the signal area still increases 20 each time. Comparing FIGS. 9B1, 9B2, and 9B3 with FIGS. 9A1, 9A2, and 9A3, it is clear that by using the nonlinear gain control method, the changes of the whole image brightness and SNR of the image are superior to the conventional linear gain control method after gain; according to FIGS. 9B1->9B2->9B3, when the gain is linearly increased, the changes of the brightness and the SNR are more even. Therefore, the present disclosure enables the output image to be clearer, and improves diagnostic accuracy.

It should be understood by persons of ordinary skill in the art that various replacements or modifications can be made to the technical solutions or inventive concepts of the present disclosure, and such modifications or replacements shall fall within the scope of the appended claims.

What is claimed is:
1. A gain control method for B-mode ultrasonic imaging, the method comprising:
receiving image data comprising a plurality of pixels;
determining an empty area of the image data comprising noise and a signal area of the image data comprising features of interest;

calculating, using a processor, a background noise threshold based on values of one or more pixels in at least one of the empty area and the signal area;

calculating, using the processor, a signal threshold based on values of one or more pixels in the signal area;

computing, using the processor, an initial gain value estimate based on an estimated uniform amplification of the image data necessary for appropriate observation of the signal of interest;

generating, using the processor, a nonlinear gain curve specifying the gain to be applied to the plurality of pixels, wherein the nonlinear gain curve specifies the gain to be applied to each pixel based on a corresponding value of the pixel, wherein the nonlinear gain curve includes:
  a first section with a first section gain between unity gain and the initial gain value estimate, wherein the first section is to be applied to pixels with pixel values between zero and the background noise threshold, and
  a second section with a second section gain greater that the initial gain value estimate when the initial gain value estimate is greater than unity gain and less than the initial gain value estimate when the initial gain value estimate is less than unity gain, wherein the second section is to be applied to pixels with pixel values between the background noise threshold and the signal threshold; and transforming, using the processor, pre-gain pixel values to post-gain pixel values using the nonlinear gain curve.

2. The gain control method for B-mode ultrasonic imaging according to claim 1, wherein the nonlinear gain curve comprises a third section with a third section gain equal to the initial gain value estimate, wherein the third section is to be applied to pixels with pixel values greater than the signal threshold.

3. The gain control method for B-mode ultrasonic imaging according to claim 1, wherein the background noise threshold and signal threshold are calculated by:
  collecting, from the image data, background noise comprising signal amplitude information from the empty area and a signal of interest comprising signal amplitude information from the signal area; and
  selecting the background noise threshold in a closed interval formed by a maximum value of the background noise and a minimum value of the signal of interest, and setting the signal threshold to be a maximum value of the signal of interest multiplied by L,
  wherein L is any number between 0 and 2.

4. The gain control method for B-mode ultrasonic imaging according to claim 3, wherein selecting the background noise threshold comprises:
  comparing the maximum value of the background noise and the minimum value of the signal of interest, and setting the maximum value of the two to be the background noise threshold.

5. The gain control method for B-mode ultrasonic imaging according to claim 3, wherein selecting the background noise threshold comprises:
  comparing the maximum value of the background noise and the minimum value of the signal, and setting the minimum value of the two to be the background noise threshold.

6. The gain control method for B-mode ultrasonic imaging according to claim 3, wherein selecting the background noise threshold comprises:
  setting the background noise threshold to be a value in an interval defined by the maximum value of the background noise and the minimum value of the signal of interest.

7. The gain control method for B-mode ultrasonic imaging according to claim 3, wherein selecting the background noise threshold comprises:
  setting the maximum value of the background noise or the minimum value of the signal of interest to be the background noise threshold.

8. The gain control method for B-mode ultrasonic imaging according to claim 1, wherein the first section of the nonlinear gain curve is obtained by generating a first gain curve comprising a line having the pre-gain pixel values as a horizontal axis, the post-gain pixel values as a vertical axis, the first section gain as a slope, and a vertical axis intercept of zero.

9. The gain control method for B-mode ultrasonic imaging according to claim 8, wherein the second section of the nonlinear gain curve is obtained by:
  generating a background noise threshold line and a signal threshold line having respective horizontal axis intercepts of the background noise threshold and the signal threshold, each line perpendicular to the horizontal axis;
  selecting an intersection of the first gain curve and the background noise threshold line to be a first intersection point, and an intersection of a standard gain curve and the signal threshold line to be a second intersection point; and
  fitting a line by connecting the first intersection point and the second intersection point, wherein the line serves as the second section of the nonlinear gain curve.

10. The gain control method for B-mode ultrasonic imaging according to claim 8, wherein the second section of the nonlinear gain curve is obtained by:
  generating a background noise threshold line and a signal threshold line having respective horizontal axis intercepts of the background noise threshold and the signal threshold, each line perpendicular to the horizontal axis;
  selecting an intersection of the first gain curve and the background noise threshold line to be a first intersection point, and an intersection of a standard gain curve and the signal threshold line to be a second intersection point; and
  fitting a curve with the first intersection point and the second intersection point, wherein the curve serves as the second section of the nonlinear gain curve.

11. The gain control method for B-mode ultrasonic imaging according to claim 10, wherein fitting the curve comprises using at lease one of a linear fitting method and a nonlinear fitting method.

12. The gain control method for B-mode ultrasonic imaging according to claim 1, wherein the first and second sections of the nonlinear gain curve are obtained by:
  generating a background noise threshold line and a signal threshold line having the pre-gain pixel values as a horizontal axis, and having respective horizontal axis intercepts of the background noise threshold and the signal threshold, each line perpendicular to the horizontal axis;
  selecting an intersection between a standard gain curve and the background noise threshold line to be a third intersection point, an intersection between the standard gain curve and the signal threshold line to be a second intersection point, and an intersection between a unity gain curve having a slope of one and the background noise threshold line to be a fourth intersection point;

selecting a fifth intersection point on the background noise threshold line between the third intersection point and the fourth intersection point; and fitting a curve through an origin where the horizontal axis intersects a vertical axis, the fifth intersection point, and the second intersection point, wherein the curve between the origin and the fifth intersection point is the first section of the nonlinear gain curve and between the fifth intersection point and the second intersection point is the second section of the nonlinear gain curve.

13. The gain control method for B-mode ultrasonic imaging according to claim 12, wherein fitting the curve comprises using at least one of a linear fitting method and a nonlinear fitting method.

14. The gain control method for B-mode ultrasonic imaging according to claim 1, wherein the first section of the nonlinear gain curve is obtained by:

generating a background noise threshold line and a signal threshold line having the pre-gain pixel values as a horizontal axis, and having respective horizontal axis intercepts of the background noise threshold and the signal threshold, each line perpendicular to the horizontal axis;

selecting an intersection of a standard gain curve and the background noise threshold line to be a third intersection point, and an intersection of a unity gain curve having a slope of one and the background noise threshold line to be a fourth intersection point;

selecting a fifth intersection point on the background noise threshold line between the third intersection point and the fourth intersection point; and fitting a curve through an origin where the horizontal axis intersects a vertical axis and the fifth intersection point, wherein the curve is the first section of the nonlinear gain curve.

15. The gain control method for B-mode ultrasonic imaging according to claim 3, wherein $L=1\pm0.2$.

* * * * *